United States Patent [19]
Molinari

[11] Patent Number: 5,247,092
[45] Date of Patent: Sep. 21, 1993

[54] PREPARATION OF THE HIGH-MELTING POLYMORPH OF TERFENADINE

[75] Inventor: Egidio Molinari, Longone Al Segrino, Italy

[73] Assignee: Erregierre Industria Chimica S.p.A., Milan, Italy

[21] Appl. No.: 653,965

[22] Filed: Feb. 12, 1991

Related U.S. Application Data

[63] Continuation-in-part of Ser. No. 500,122, Mar. 28, 1990, abandoned.

[30] Foreign Application Priority Data

Dec. 29, 1989 [IT] Italy ................................ 22874 A/89

[51] Int. Cl.$^5$ ........................................... C07D 211/22
[52] U.S. Cl. ................................................ 546/241
[58] Field of Search ........................................ 546/241

[56] References Cited

U.S. PATENT DOCUMENTS 4,742,175 5/1988 Fawcett et al. ..................... 546/241

FOREIGN PATENT DOCUMENTS 0396100 11/1990 European Pat. Off. .

*Primary Examiner*—C. Warren Ivy
*Assistant Examiner*—Phyllis G. Spivack
*Attorney, Agent, or Firm*—Birch, Stewart, Kolasch & Birch

[57] ABSTRACT

A process for preparing the high-melting polymorph of terfenadine, characterized by dissolving terfenadine in a water-miscible polar solvent by heating to a temperature of between 40° and 100° C. The solution is then percolated into a sufficient quantity of water, kept stirring at ambient temperature, to cause substantial precipitation of the high-melting terfenadine polymorph.

5 Claims, No Drawings

PREPARATION OF THE HIGH-MELTING POLYMORPH OF TERFENADINE

This application is a continuation-in-part of application Ser. No. 07/500,122 filed on Mar. 28, 1990 now abandoned.

FIELD OF THE INVENTION

This invention relates to a process for preparing a high-melting polymorph of terfenadine, that is, α-(p-tert.butylphenyl)-4-(hydroxydiphenylmethyl)-1-piperidine butanol.

BACKGROUND OF THE INVENTION

Terfenadine is a pharmaceutical product with an antihistaminic activity.

Processes for preparing terfenadine are known and are described, for example, in Italian patent application 21674 A/87 filed on May 25, 1987 by the present applicant.

It is also known, as described in U.S. Pat. No. 4,742,175, that terfenadine crystallizes in two different polymorphic forms, and can be prepared in the form of the high-melting and the low-melting polymorphic product. The low-melting polymorph has a melting point of 146° C. The high-melting polymorph, which is also the product mostly requested by the pharmaceutical industry, has a melting point range of 149°–151° C.

SUMMARY OF THE INVENTION

The present invention provides a process for selectively producing the high-melting polymorph of terfenadine at high purity and with a very short preparation time and very low production costs.

According to the present invention the crude terfenadine is dissolved in a polar solvent miscible with water. The solution is heated to between 40° and 100° C. to completely dissolve the product, filtered while hot to remove any solid impurities, and then added to a suitable volume of water kept at ambient temperature and stirred, to precipitate the high-melting terfenadine.

The amount of water is at least 2 parts by volume per part of solution. Higher amounts of water and generally up to 10 parts by volume can be used. Amounts higher than 10 volumes are not useful from an economical point of view because large size apparatus would be necessary. Water-miscible polar solvents which can be advantageously used in the process of the invention are selected from the group consisting of N,N-dimethylformamide, dioxane, acetone, 2-methoxyethanol (methyl cellosolve), acetonitrile, methylacetate, ethylacetate, tetrahydrofurane, N,N-dimethyl-acetamide, dimethoxyethane (glyme), diethylenglycol-dimethylether (diglyme) and mixtures of the above solvents can be used.

DETAILED DESCRIPTION OF THE INVENTION

It has been found that if the terfenadine is precipitated in the above defined working conditions (i.e. by adding to water the terfenadine dissolved in an organic solvent rather than vice versa), the following advantages are obtained:

the high-melting terfenadine precipitates easily at ambient temperature;

the precipitation is rapid and complete and a lengthy crystallization time is not required;

the filtration for recovering the precipitate can be carried out at ambient temperature without the need to cool the mixture to between 0° and 5° C.

The solution containing terfenadine is added to the water preferably slowly.

The suspension thus obtained is filtered at ambient temperature and the pure high-melting polymorphic product is washed with water and dried by conventional methods, for example, under vacuum at a temperature not exceeding 60° C.

The product obtained by the process according to the present invention has a high degree of purity.

In addition the time required for the purification process is very short, and thus the process is extremely advantageous from the view point of cost.

Some examples of the preparation of the high-melting polymorph of terfenadine are given hereinafter by way of non-limiting examples.

EXAMPLE 1

50 g of crude terfenadine are placed in a two-neck flask fitted with a stirrer and reflux condenser, dispersed with 100 ml of N,N-dimethylformamide and then heated to 80° C. to completely dissolve the product.

The solution is filtered hot and transferred into a funnel fitted with a cock, by which it is dripped into 400 ml of deionized water at ambient temperature while stirring continuously (the addition takes about 30 minutes).

After cooling to ambient temperature, the suspension obtained is filtered and the product washed with two 100 ml portions of water and dried under vacuum at 60° C.

About 48.7 grams of pure high-melting polymorphic product are obtained with a melting point of 150°–151° C.

EXAMPLE 2

50 g of crude terfenadine are placed in a two-neck flask fitted with a stirrer and reflux condenser, dispersed with 250 ml of dioxane and then heated to 80° C. to completely dissolve the product.

The solution is filtered hot and transferred into a funnel fitted with a cock, by which it is dripped into 2 liters of deionized water at ambient temperature while stirring continuously (the addition takes about 60 minutes).

After cooling to ambient temperature, the suspension obtained is filtered and the product washed with two 100 ml portions of water and dried under vacuum at 60° C.

About 49 grams of pure high-melting polymorphic product are obtained with a melting point of 149°–150° C.

EXAMPLE 3

50 g of crude terfenadine are placed in a two-neck flask fitted with a stirrer and reflux condenser, dispersed with 250 ml of acetone, and heated under reflux to completely dissolve the product.

The solution is filtered hot and transferred into a funnel fitted with a cock, by which it is dripped into 1250 ml of deionized water at ambient temperature while stirring continuously (the addition takes about 60 minutes).

After cooling to ambient temperature, the suspension obtained is filtered and the product washed with two 100 ml portions of deionized water and dried under vacuum at 60° C.

49.5 grams of pure high-melting polymorphic product are obtained with a melting point of 150°-151° C.

EXAMPLE 4

50 g of crude terfenadine are placed in a two-neck flask fitted with a stirrer and reflux condenser, dispersed with 200 ml of 2-methoxyethanol (methyl cellosolve), and heated to 80° C. to completely dissolve the product.

The solution is filtered hot and transferred into a funnel fitted with a cock, by which it is dripped into 1600 ml of deionized water while stirring continuously (the addition takes about 60 minutes). After cooling to ambient temperature, the suspension obtained is filtered and the product washed with two 100 ml portions of deionized water and dried under vacuum at 60° C.

49.4 grams of pure high-melting polymorphic product are obtained with a melting point of 150°-151° C.

EXAMPLE 5

50 g of crude terfenadine are placed in a two-neck flask fitted with a stirrer and reflux condenser, dispersed with 250 ml of acetonitrile, heating under reflux to completely dissolve the product. The solution is filtered hot and transferred into a funnel fitted with a cock, by which it is dripped into 1250 ml of deionized water at ambient temperature while stirring continuously (the addition takes about 60 minutes).

After cooling to ambient temperature, the suspension obtained is filtered and the product washed with two 100 ml portions of deionized water and dried under vacuum at 60° C.

49.2 grams of pure high-melting polymorphic product are obtained with a melting point of 150°-151° C.

I claim:

1. A process for preparing the high-melting polymorph of terfenadine, which comprises dissolving terfenadine in a solvent selected from the group consisting of N,N-dimethylformamide, dioxane, acetone, methyl cellosolve, acetonitrile, methylacetate, ethylacetate, tetrahydrofurane, N,N-dimethylacetamide, dimethoxyethane, diethylenglycol-dimethylether and mixture thereof, to form a solution by heating to a temperature between 40° and 100° C. then pouring said solution into at least two parts by volume of water per part of solution, while stirring at room temperature, to cause substantial precipitation of the high melting terfenadine polymorph, and finally separating the precipitate.

2. The process as claimed in claim 1, wherein the solution containing terfenadine is filtered at the same temperature of the dissolution step before being poured into the water, so as to remove any solid bodies present.

3. The process as claimed in claim 1, wherein after filtration, the precipitated high-melting terfenadine polymorph is washed with water at ambient temperature.

4. The process as claimed in claim 1, wherein said solution is poured into said water at room temperature over about 30 to 60 minutes.

5. A process for preparing the high-melting polymorph of terfenadine, which comprises dissolving terfenadine in a solvent selected from the group consisting of N,N-dimethylformamide, dioxane, acetone, methyl cellosolve, acetonitrile, methylacetate, ethylacetate, tetrahydrofurane, N,N-dimethylacetamide, dimethoxyethane, diethylenglycol-dimethylether and mixtures thereof, to form a solution by heating to a temperature between 40° and 100° C. then adding solution into at least two parts by volume of water per part of solution during a 30-60 minute period, while stirring at room temperature, to cause substantial precipitation of the high melting terfenadine polymorph, washing the precipitated high-melting terfenadine polymorph with water at ambient temperature after filtering the precipitated high-melting terfenadine polymorph, and separating the precipitate.

* * * * *